(12) United States Patent
Stone

(10) Patent No.: US 8,197,482 B2
(45) Date of Patent: Jun. 12, 2012

(54) APPARATUS FOR FORMING A TUNNEL IN A BONE

(75) Inventor: Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 167 days.

(21) Appl. No.: 12/828,957

(22) Filed: Jul. 1, 2010

(65) Prior Publication Data

US 2010/0268233 A1 Oct. 21, 2010

Related U.S. Application Data

(63) Continuation of application No. 11/526,173, filed on Sep. 22, 2006, now Pat. No. 7,749,226.

(51) Int. Cl.
*A61B 17/00* (2006.01)

(52) U.S. Cl. .......................................................... 606/80

(58) Field of Classification Search .................... 606/96, 606/67, 79, 86 R–90, 95, 98, 80
See application file for complete search history.

(56) References Cited

U.S. PATENT DOCUMENTS

| | | |
|---|---|---|
| 4,744,353 A | 5/1988 | McFarland |
| 4,787,377 A | 11/1988 | Laboureau et al. |
| 4,872,451 A | 10/1989 | Moore et al. |
| 4,883,048 A | 11/1989 | Purnell et al. |
| 5,147,367 A | 9/1992 | Ellis |
| 5,207,753 A | 5/1993 | Badrinath |
| 5,314,429 A | 5/1994 | Goble |
| 5,385,567 A | 1/1995 | Goble |
| D357,534 S | 4/1995 | Hayes |
| D359,557 S | 6/1995 | Hayes |
| 5,562,673 A | 10/1996 | Koblish et al. |
| 5,643,273 A | 7/1997 | Clark |
| 5,755,718 A * | 5/1998 | Sklar ............................ 606/80 |
| D398,996 S | 9/1998 | Simmons et al. |
| 6,022,356 A | 2/2000 | Noyes et al. |
| 6,030,401 A | 2/2000 | Marino |
| D433,506 S | 11/2000 | Asfora |
| 6,200,322 B1 | 3/2001 | Branch et al. |
| 6,537,319 B2 | 3/2003 | Whelan |
| 6,755,840 B2 | 6/2004 | Boucher et al. |
| 6,878,150 B1 | 4/2005 | McGuire et al. |
| 7,090,677 B2 * | 8/2006 | Fallin et al. ..................... 606/80 |
| 7,255,702 B2 | 8/2007 | Serra et al. |
| 7,749,226 B2 | 7/2010 | Stone |
| 2002/0173795 A1 * | 11/2002 | Sklar ............................ 606/80 |
| 2004/0059339 A1 * | 3/2004 | Roehm et al. ................. 606/90 |
| 2004/0092950 A1 | 5/2004 | Pohjonen et al. |
| 2005/0107800 A1 | 5/2005 | Frankel et al. |
| 2005/0177171 A1 | 8/2005 | Wetzler et al. |

OTHER PUBLICATIONS

"Inventing the Future of Arthroscopy", Arthrotek, Inc., 2004. cited by other.

(Continued)

*Primary Examiner* — Thomas C. Barrett
*Assistant Examiner* — Sameh Boles
(74) *Attorney, Agent, or Firm* — Harness, Dickey

(57) ABSTRACT

An apparatus and method for forming a tunnel in a bone. The apparatus is used to form a first tunnel in the bone, the tunnel having a longitudinal axis, inserting a first drill guide into the first tunnel, supporting a first tunnel-forming device along an axis defining a first offset relative the longitudinal axis of the first tunnel with the first drill guide, and forming a second tunnel alongside the first tunnel with the first tunnel-forming device, the second tunnel communicating with the first tunnel and defining a single elongated opening.

16 Claims, 7 Drawing Sheets

OTHER PUBLICATIONS

Fanelli, Gregory C., M.D., "Fanelli PCL/ACL Guide, Rationale and Surgical Technique", Arthrotek, Inc., 2002. cited by other.

Howell, M.D., Stephen M., "Howell 65.degree. Tibial Guide", Arthrotek, Inc., 2002. cited by other.

* cited by examiner

APPARATUS FOR FORMING A TUNNEL IN A BONE

CROSS-REFERENCE TO RELATED APPLICATIONS

This application is a continuation of U.S. patent application Ser. No. 11/526,173 filed on Sep. 22, 2006. The entire disclosure of the above application is incorporated herein by reference.

INTRODUCTION

During anterior or posterior cruciate ligament reconstruction surgery for the knee, femoral and tibial tunnels are drilled for securing a graft ligament to the tibia and femur. Various drill guides or aimers are known for guiding a drilling device to form these tunnels.

Although the existing drill guides can be satisfactory for their intended purposes, there is still a need for additional procedures and devices that facilitate drilling femoral and tibial bone tunnels.

SUMMARY

The present teachings provide a method for forming a tunnel in a bone. The method includes forming a first tunnel in the bone, the tunnel having a longitudinal axis, inserting a first drill guide into the first tunnel, supporting a first tunnel-forming device along an axis defining a first offset relative the longitudinal axis of the first tunnel with the first drill guide, and forming a second tunnel alongside the first tunnel with the first tunnel-forming device, the second tunnel communicating with the first tunnel and defining a single elongated opening.

The present teachings also provide a method for forming a tunnel in a bone and includes forming a first tunnel in the bone, the first tunnel having a longitudinal axis, inserting into the first tunnel a first drill guide having a guiding bore with an axis defining a first offset relative to the longitudinal axis of the first tunnel, supporting a first tunnel-forming device on the first drill guide such that a longitudinal axis of the first tunnel-forming device coincides with the axis of the guiding bore and the first tunnel-forming device extends at least partially outside the first tunnel in a transverse direction relative to the longitudinal axis of the first tunnel, and drilling with the first tunnel-forming device a second tunnel parallel to and communicating with the first tunnel along the longitudinal direction.

The present teachings further provide a method for forming a tunnel in a bone. The method includes inserting a guide pin in the bone, positioning a cannulated tunnel-forming device over the guide pin, drilling with the cannulated tunnel-forming device a first tunnel in the bone, the first tunnel having a longitudinal axis, and removing the guide pin and the cannulated tunnel-forming device. The method further includes inserting into the first tunnel a first drill guide having a guiding bore with an axis defining a first offset relative to the longitudinal axis of the first tunnel, supporting a first tunnel-forming device on the first drill guide such that a longitudinal axis of the first tunnel-forming device coincides with the axis of the guiding bore and the first tunnel-forming device extends at least partially outside the first tunnel in a transverse direction relative to the longitudinal axis of the first tunnel, and drilling with the first tunnel-forming device a second tunnel parallel to and communicating with the first tunnel along the longitudinal direction and in the direction of the offset, wherein the first and second tunnels define an elongated opening, the elongated opening being elongated in the direction of the first offset.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses. For example, although the present teachings are illustrated for cruciate ligament reconstruction in knee surgery, the present teachings can be used for re-shaping any tunnel in a long bone, including the tibia and femur.

Figures 11, 12:
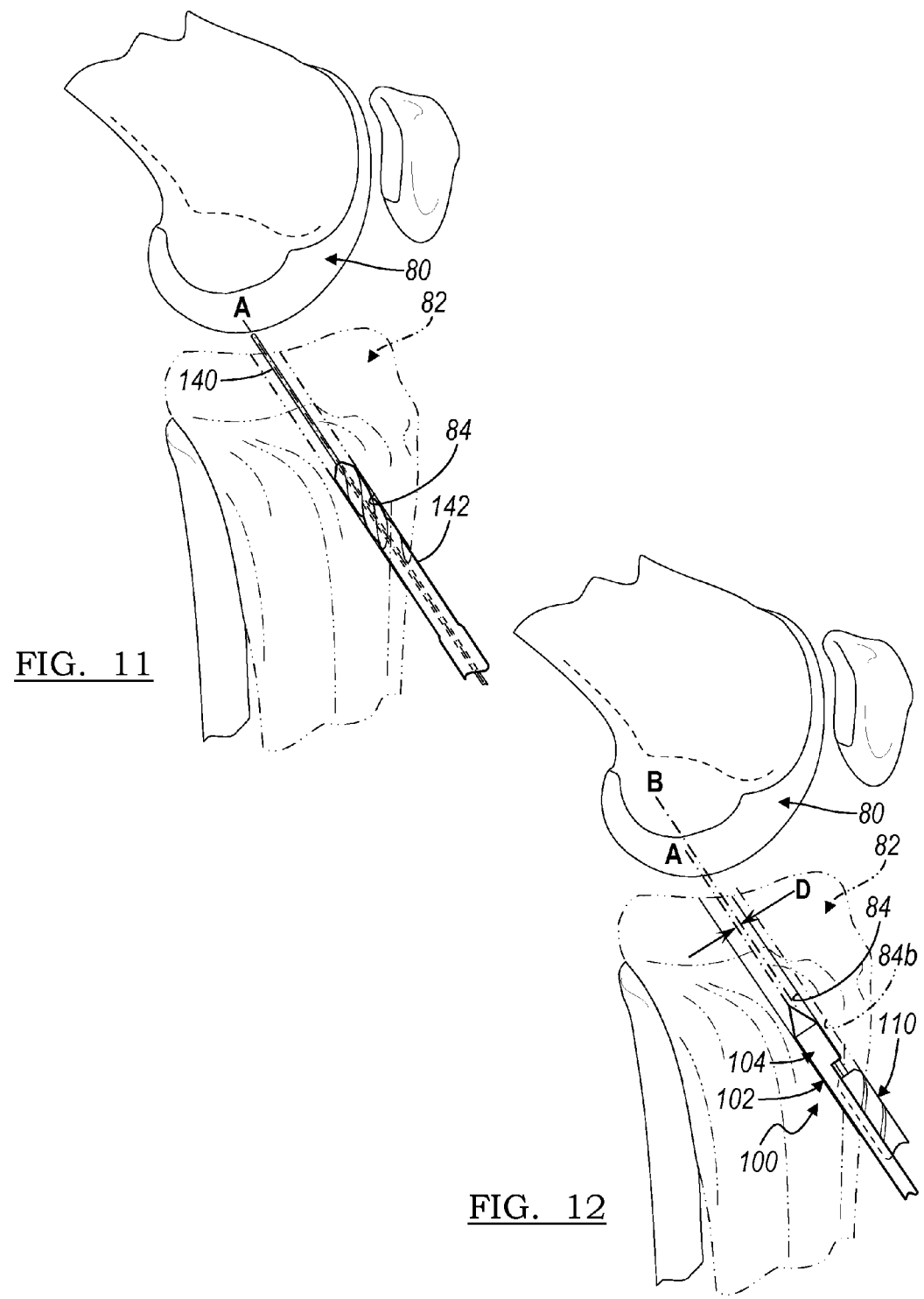
FIG. 11 is an environmental view showing a cannulated tunnel-forming device over a guide pin in a tibial tunnel.
FIG. 12 is an environmental view showing the drill guide device of FIG. 5 in a tibial tunnel.
Figure 14:
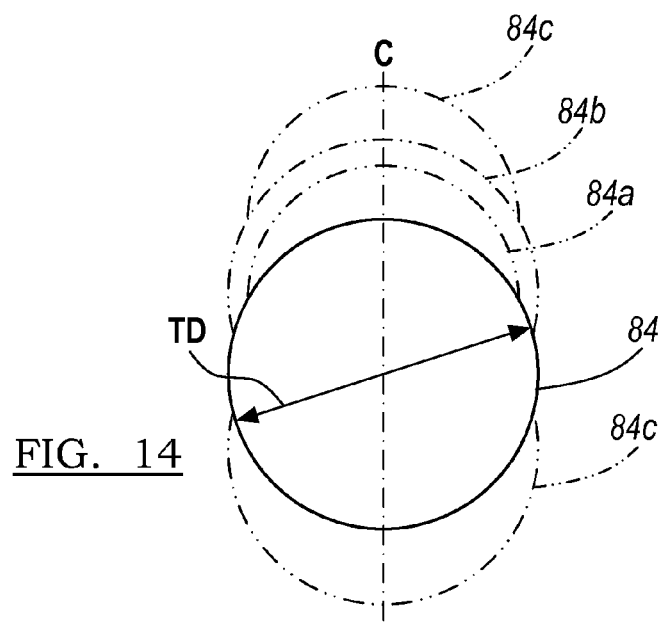
FIG. 14 is a view showing exemplary cross-sections of a bone tunnel formed according to the present teachings.

Referring to FIGS. 1-7, 11, 12 and 14, an exemplary drill guide device 100 according to the present teachings can be used to change the shape of an existing or first bone tunnel 84 during cruciate ligament reconstruction. The first bone tunnel 84 can have substantially circular cross-section and can be initially drilled over a guide wire or a guide pin 140 in the tibia 82 or femur 80 by conventional methods using, for example, a cannulated tunnel-forming device 142, as shown in FIG. 11. The guide wire 140 and the cannulated tunnel-forming device 142 can then be removed. The drill guide device 100 can be used to change the shape of the cross-section of the first bone tunnel 84 from circular to oval, egg-shaped, pear-shaped, elongated, eight-shaped, or asymmetric in a desired orientation including the anterior, posterior, medial or lateral directions, or any other shape, as discussed below. The drill guide device 100 can be used after such change in the shape of the first bone channel 84 is made to further change the new cross-section, as discussed below. The new shape of the first bone tunnel 84 can be selected for providing a desired anatomic orientation, path/shape and placement of the ligament grafts, as determined by the surgeon. For example, bone tunnels with elongated cross-sections can be used for accommodating several strands of ligament grafts, and can also be used to approximate the shape and path of the anterior or posterior cruciate ligaments. The elongated shape can be made by drilling a new tunnel alongside and communicating with first bone tunnel 84 as illustrated in FIG. 14, and discussed below.

The drill guide device 100 can include an arm 102, a drill guide 104 extending from the arm 102, and a support member 106, which can be used to secure the drill guide device 110 to the bone and can also function as a handle. The support member 106 can have first and second portions 106a and 106b. The arm 102 can be supported either fixedly or removably on its proximal end on the first portion 106a of the support member 106 at an angle of about 90-degrees for exerting axial force. The second portion 106b can be oriented at a different angle relative to the arm 102, for ergonomic considerations and for avoiding the patient's anatomy. The arm 102 can be in the form of a semi-cylindrical shaft having an open-channel cross-section 116 or as an incomplete/open tube, adapted for receiving and guiding a drill, any other drilling/reaming device, a trephine, or generally any tunnel-forming device 110, such that a portion of the tunnel-forming device extends outside the cross-section 116 of the arm 102 to be exposed to form the tunnel.

Figure 1:
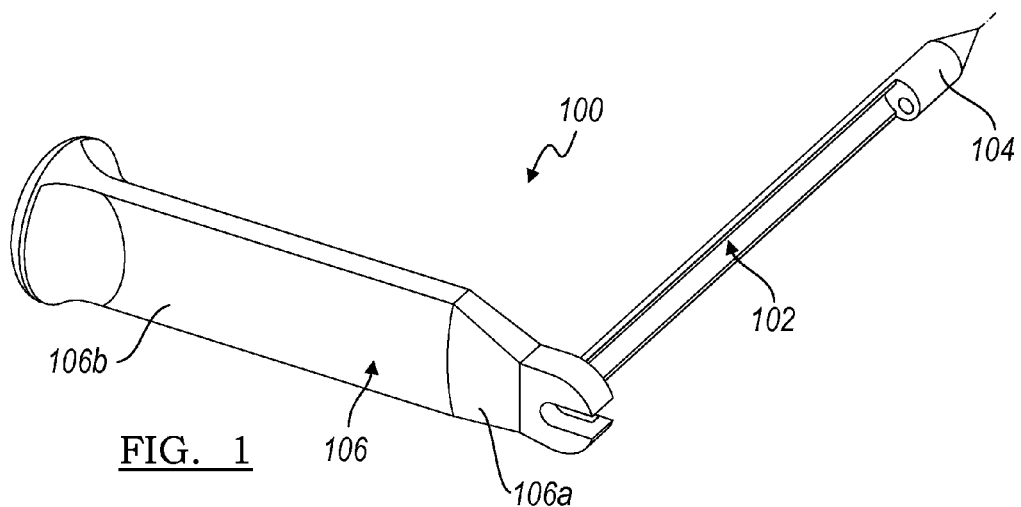
FIG. 1 is a perspective view of a drill guide device according to the present teachings.
Figure 2:
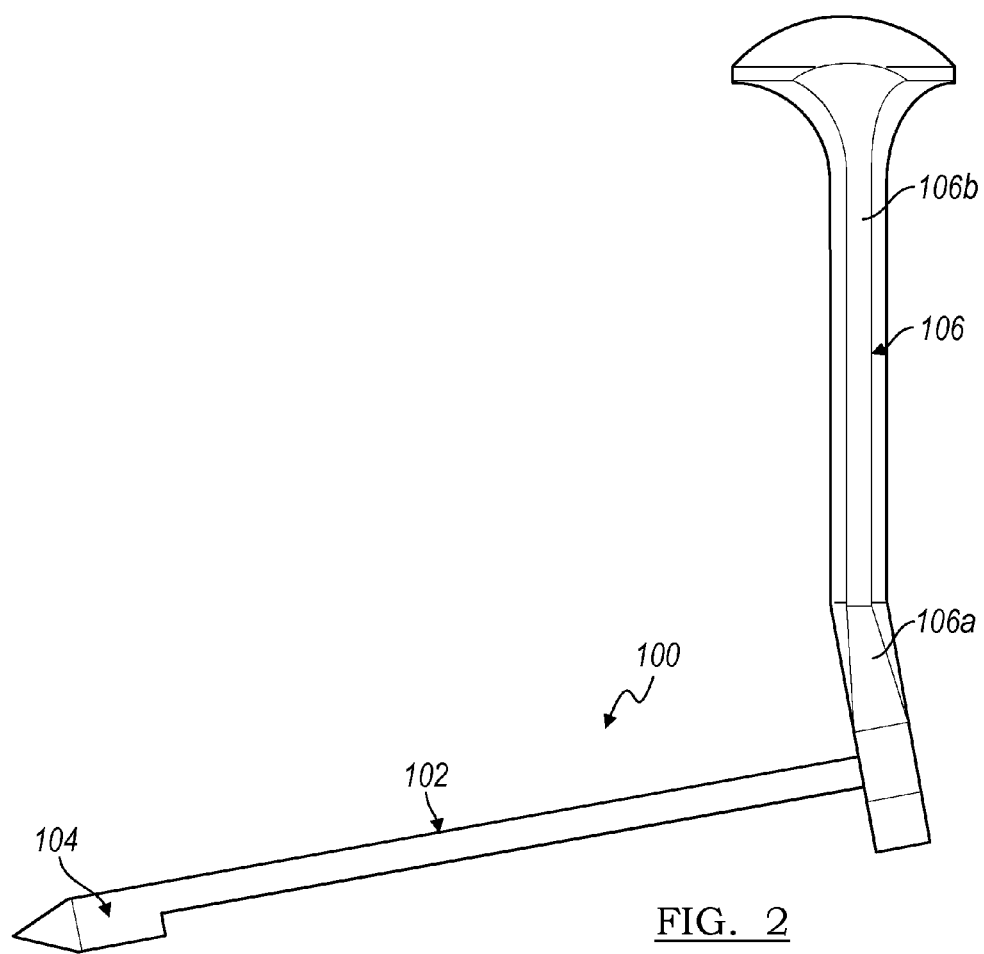
FIG. 2 is a side view of the drill guide device of FIG. 1.
Figure 3:
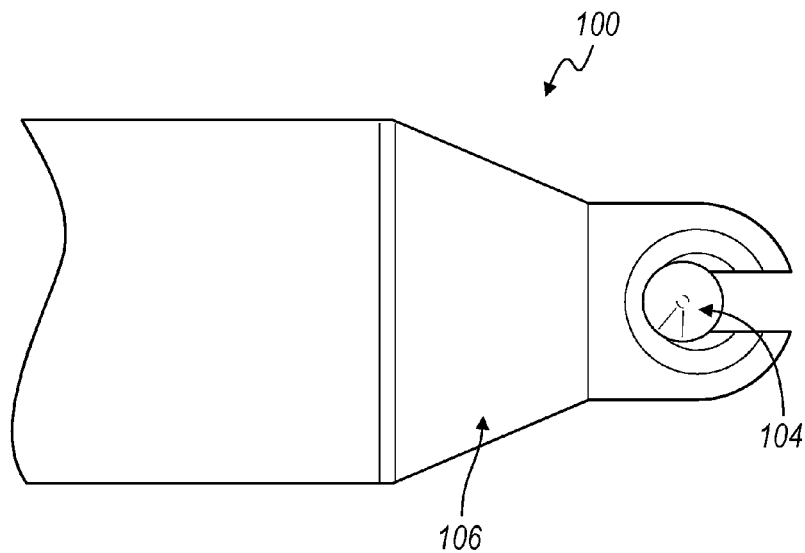
FIG. 3 is front view of the drill guide device of FIG. 1.
Figure 4:
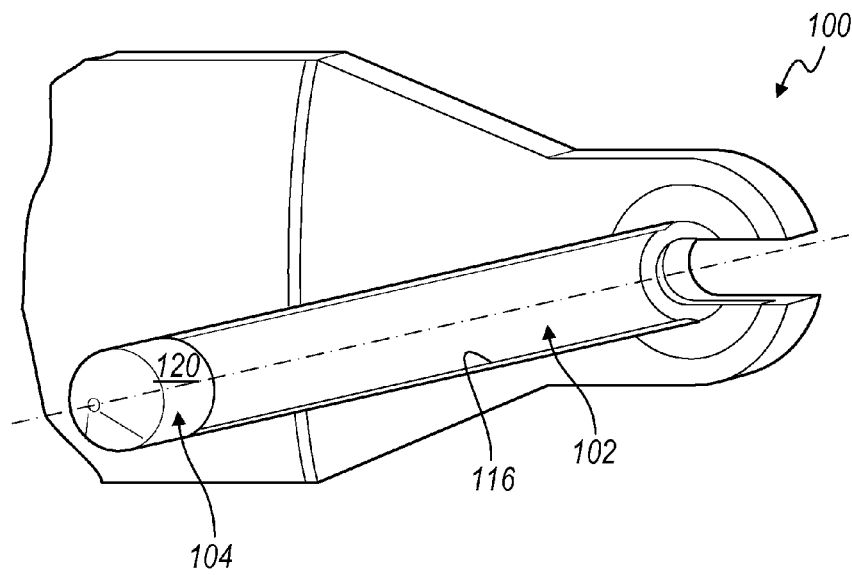
FIG. 4 is another a perspective view of the drill guide device of FIG. 1.
Figure 6:
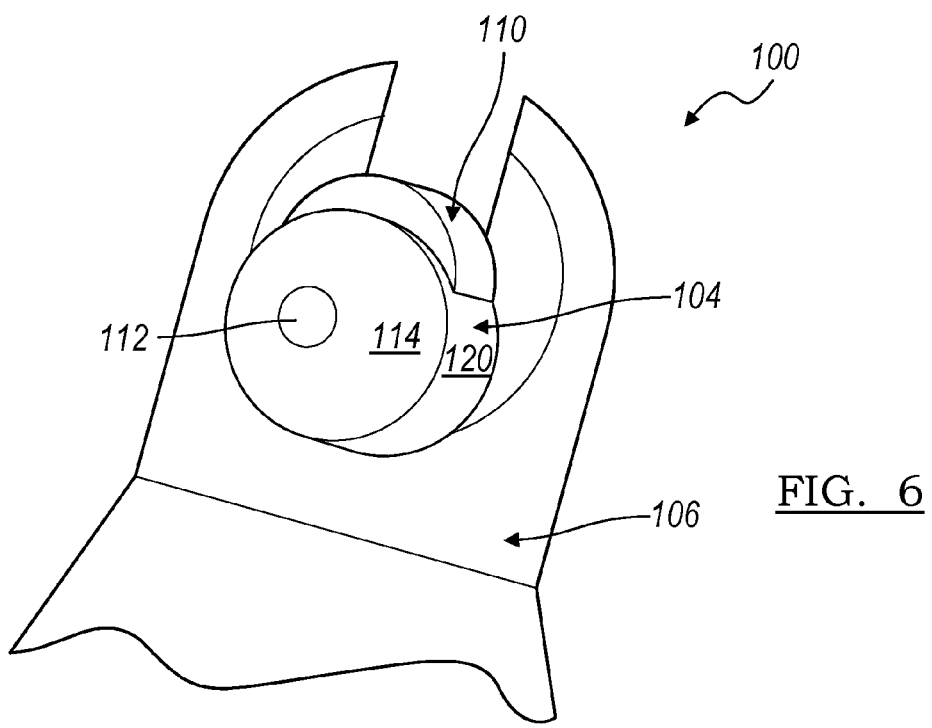
FIG. 6 is a front perspective view of the drill guide device of FIG. 5.
Figure 7:
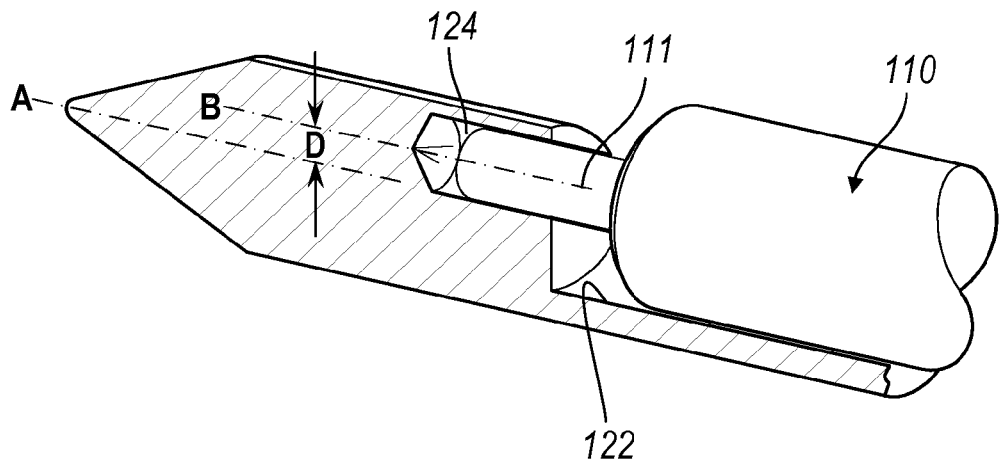
FIG. 7 is a sectional view of the drill guide device of FIG. 5.
Figure 8:
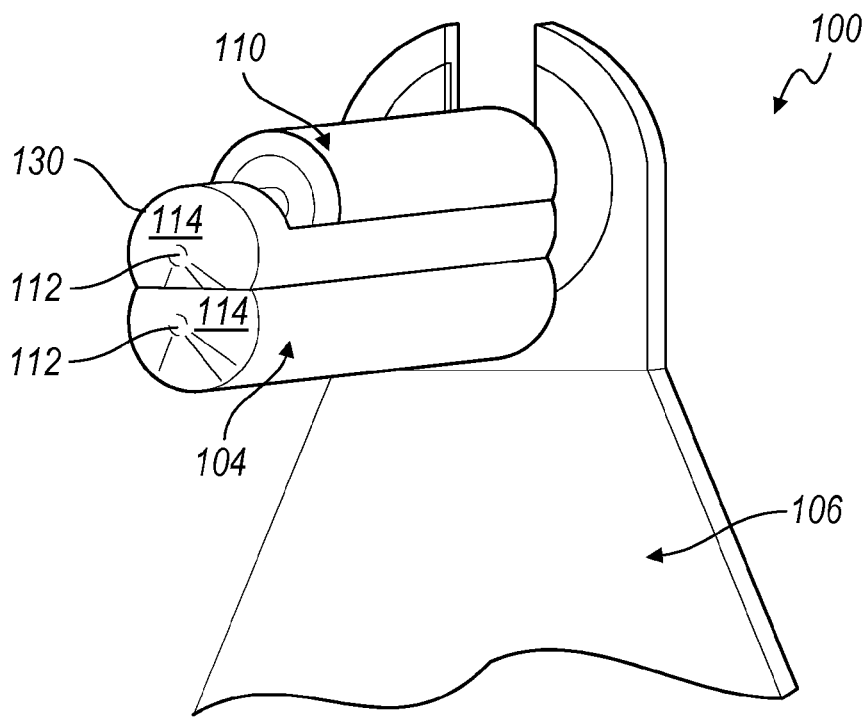
FIG. 8 is a side perspective view of a drill guide device according to the present teachings, the drill guide device shown with a tunnel-forming device.

Referring to FIGS. 4 and 6, the drill guide 104 can be bullet-shaped, and include a proximal portion 120 and a distal portion 114, which is first inserted into the bone tunnel. The proximal portion 120 can be cylindrical, and the distal portion 114 can be conical with a blunt closed tip 112. The proximal portion 120 can have a cross-section in the form of a complete circle, as shown in FIG. 4, or can be a portion of a circle with an arc cut off as shown in FIG. 6.

Figure 5:
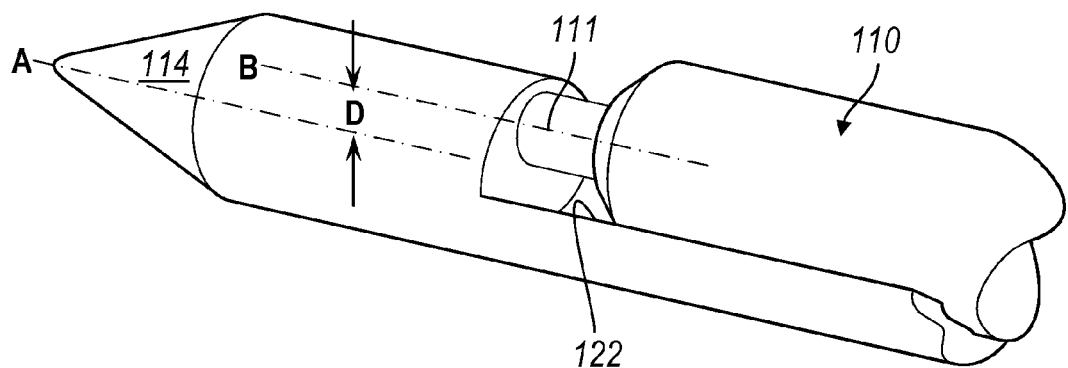
FIG. 5 is a side perspective view of a drill guide device according to the present teachings, the drill guide device shown with a tunnel-forming device.

The outer surface of the first portion 120 can substantially conform to the shape of the first bone tunnel 84. If the first bone tunnel 84 is circular, then the drill guide 100 can have a circular cross-section with a diameter that corresponds to the diameter of the bone tunnel 84, such that the drill guide 104 can be inserted in the first bone tunnel 84. The proximal and distal portions 120, 114 of the drill guide 104 are concentric and define a longitudinal axis A that substantially coincides with the bone tunnel axis when the drill guide 104 is inserted into the bone tunnel 84, as illustrated in FIG. 12. A tunnel-forming device having a longitudinal drill axis B can seat on an inner surface 122 of the arm 102 and be guided by the drill guide 104, as shown in FIGS. 5 and 6, such that the drill axis B is parallel and offset relative to the axis A by an offset distance D. The tunnel-forming device can include a distal shaft 111, which can be received in an internal guiding bore 124 of the drill guide 104. The guiding bore 124 defines an axis B which coincides with the drill axis B. The offset D allows the tunnel-forming device to extend the diameter TD of the bone tunnel 84 in a selected direction C to define a new cross-section that is elongated in the direction of the axis C, such as the exemplary cross-sectional shapes shown at 84a, 84b in FIG. 14. The new cross-sectional shape can be any shape with an elongated axis, including eight-shaped, oval, pear or egg-shaped and other elongated shapes with one or two axes of symmetry.

Figure 9:
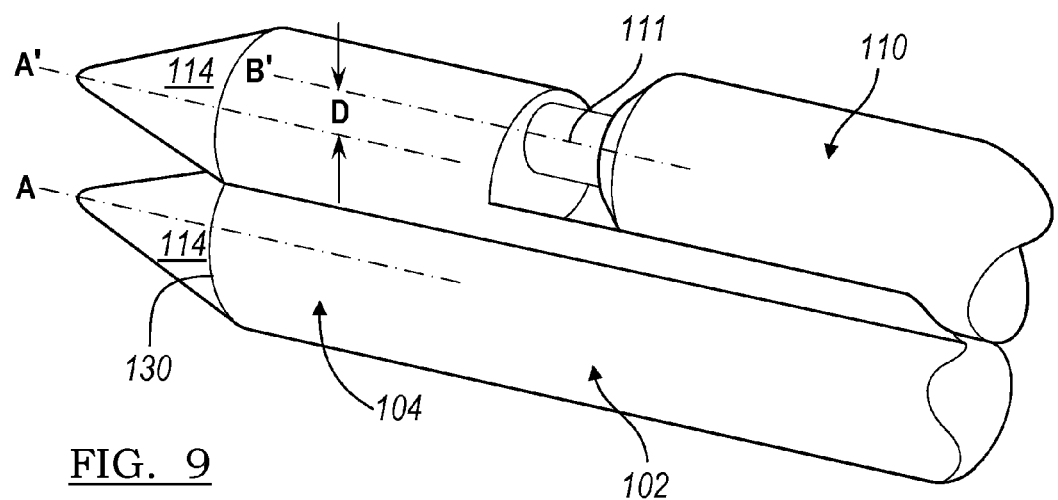
FIG. 9 is a front perspective view of the drill guide device of FIG. 8.
Figure 10:
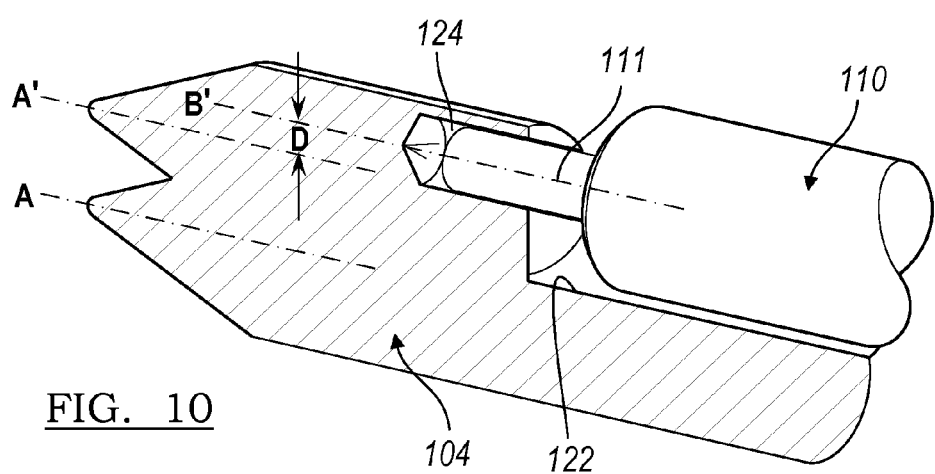
FIG. 10 is a sectional view of the drill guide device of FIG. 8.

Referring to FIGS. 8-10, 13 and 14, the drill guide device 100 can include a drill guide 104 that can be used with a second bone tunnel 84b that has already been elongated in the direction C, as discussed above. The drill guide 104 can have a cross-sectional shape 130 that corresponds to the elongated shape of the second tunnel 84b, such that the drill guide 104 can be inserted in the second bone tunnel 84b for elongating further the second bone tunnel 84b to a third bone tunnel 84c with a new shape. For example, the drill guide 104 can include first and second distal portions 114 arranged one above the other and having corresponding longitudinal axes A and A', as shown in FIG. 9. The first and second distal portions 114 can be made as single unitary part of the drill guide or can be separate, but modularly connected portions. A guiding bore 124 in the drill guide 104 defines an axis B' which coincides with the drill axis and is offset from the second axis A' by an offset distance D. It should be appreciated that the offset distance D can have many different values and is not necessarily equal to the offset distance D between axes A and B shown in FIG. 7. Further, the additional elongation of the tunnel 84b to a new tunnel 84c can be provided in the same, opposite or other different direction than the direction of the initial elongation, as shown, for example, in FIG. 14, which illustrated two elongations 84c in opposite directions relative to the first bone tunnel 84.

Referring to FIGS. 12 and 14, a first drill guide 104 with a single drill guide axis A, such as the one shown in FIG. 5, is inserted in a first bone tunnel 84 of circular cross-section, which was formed, for example, as discussed above in connection with FIG. 11. The first drill guide 104 can align a first tunnel-forming device along an axis B parallel and offset by a distance D from the drill guide axis A, such that the first tunnel-forming device extends at least partially outside the first bone tunnel 84 in a direction transverse to the axis A, which also coincides with the longitudinal axis of the first bone tunnel 84. The first tunnel-forming device can be operated to drill another tunnel alongside and communicating with the first tunnel 84 such that the resulting new tunnel defines a second bone tunnel 84b with an elongated opening. The first drill guide 104 and the first tunnel-forming device are then removed.

Figure 13:
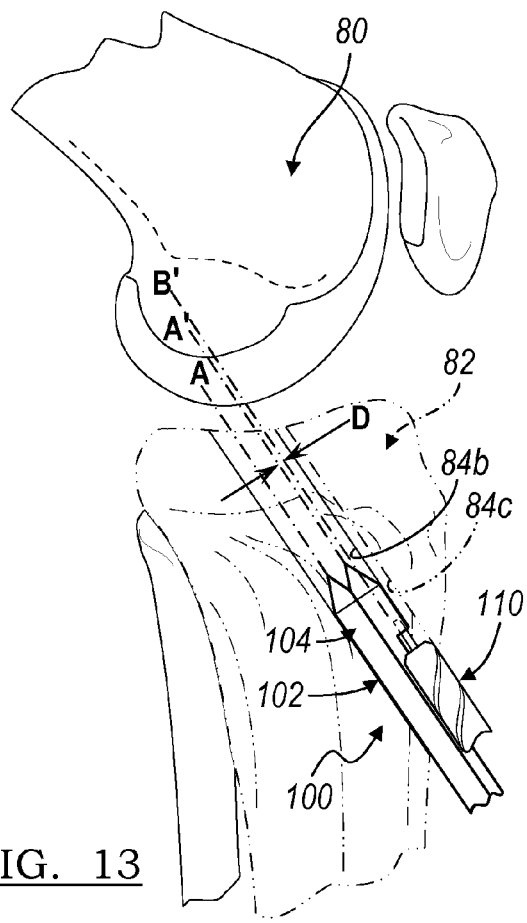
FIG. 13 is an environmental view showing the drill guide device of FIG. 8 in a tibial tunnel.

Referring to FIGS. 12 and 13, a second drill guide 104 with first and second parallel axes A, A' can be inserted in a second bone tunnel 84b that has an elongated cross-section. The elongated cross-section of the second bone tunnel 84b can be created as discussed above in connection with FIG. 11. A second tunnel-forming device is guided along an axis B' which is offset from the second axis A' by an offset distance D, such that the second tunnel-forming device extends at least partially outside the second bone tunnel 84b in a direction transverse to the axes A and A'. The offset distance D can further elongate the second bone tunnel 84b to a third bone tunnel 84c that has a more elongated cross-section. The second tunnel-forming device can be the same as the first tunnel-forming device, or can be a different tunnel-forming device having a different diameter.

It will be appreciated that although methods according to the present teachings are illustrated in FIGS. 11-13 in relation to a tibia, the present teachings are similarly applicable in relation to other bones, including the femur. Further, although a few exemplary shapes of bone tunnels elongated in one direction and its opposite are illustrated in FIG. 14, other shapes elongated in different directions other than the direction C and its opposite, can be similarly obtained, including elongations in the anterior, posterior, lateral or medial directions of the bone. Such shapes can be used to accommodate the path and orientations of multiple cruciate ligament grafts without unduly interfering with the patient's anatomy or occupying excessive bulk in comparison with circular cross-sections sized to accommodate several strand of ligament grafts. Variations of the shape of the bone tunnel can be obtained by varying, for example, the amount of each offset, the diameter of the tunnel-forming device used for each offset, at least one diameter of each drill guide, or the direction of each offset.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An apparatus for forming a tunnel in a bone comprising: a drill guide having a unitary body, the unitary body including a first tapered portion having a first longitudinal axis, a second tapered portion integrally attached to the first tapered portion, a cylindrical segment extending from the first tapered portion and from the second tapered portion and an arm with an open channel, the arm extending from the cylindrical segment, the cylindrical segment defining a blind guiding bore centered about a second longitudinal axis, the second longitudinal axis parallel and offset relative to the first longitudinal axis; and a tunnel-forming device having a first portion received in the blind guiding bore and a second portion supported on the open channel of the arm, the tunnel-forming device centered about a longitudinal drill axis coinciding with the second longitudinal axis, wherein the second portion of the tunnel-forming device extends beyond a cross-section of the cylindrical segment for forming a tunnel in a bone about the longitudinal drill axis.

2. The apparatus of claim 1, wherein the open channel of the arm is semi-cylindrical.

3. The apparatus of claim 1, wherein the cylindrical segment of the drill guide has a circular cross-section.

4. The apparatus of claim 1, wherein the cylindrical segment has an elongated cross-section.

5. The apparatus of claim 4, wherein the elongated cross-section is oval.

6. The apparatus of claim 4, wherein the elongated cross-section is eight-shaped.

7. An apparatus for forming a tunnel in a bone comprising: a unitary drill guide having a first tapered portion having a first longitudinal axis and a second tapered portion integrally attached to the first tapered portion, the second tapered portion having a second longitudinal axis parallel to the first longitudinal axis; and a tunnel-forming device supported on the drill guide and centered about a drill axis that is parallel and offset relative to the first longitudinal axis, wherein the drill guide includes a cylindrical segment with a first portion extending from the first tapered portion and a second portion parallel to the first portion and extending from the second tapered portion, wherein the drill guide includes an arm extending from the cylindrical segment, the arm forming an open channel supporting the tunnel-forming device, wherein the tunnel-forming device extends beyond the cross-section of the cylindrical segment for forming a tunnel in a bone about the drill axis.

8. The apparatus of claim 7, wherein the first portion of the cylindrical segment defines a guiding bore having a longitudinal axis coinciding with the drill axis of the tunnel-forming device.

9. The apparatus of claim 7, wherein the first portion of the cylindrical segment defines a guiding bore receiving a portion of the tunnel-forming device along the drill axis.

10. The apparatus of claim 7, wherein the cylindrical segment has an elongated cross-section.

11. The apparatus of claim 7, wherein the cylindrical segment has an eight-shaped cross-section.

12. An apparatus for forming a tunnel in a bone comprising: a drill guide having a unitary body, wherein the unitary body includes a first tapered portion having a first longitudinal axis and a second tapered portion integrally attached to the first tapered portion, the second tapered portion having a second longitudinal axis parallel to the first longitudinal axis, the unitary body of the drill guide having a cylindrical segment extending from the first and second tapered portions and having an elongated cross-section, the cylindrical segment defining a blind guiding bore centered about a third longitudinal axis, the third longitudinal axis parallel and offset relative to the first longitudinal axis; and a tunnel-forming device having a first portion received in the blind guiding bore, the tunnel-forming device centered about a longitudinal drill axis coinciding with the third longitudinal axis, wherein the tunnel-forming device extends beyond the cross-section of the cylindrical segment for forming a tunnel in a bone about the drill axis.

13. The apparatus of claim 12, wherein the cylindrical segment includes a first portion extending from the first tapered portion and a second portion extending from the second tapered portion, and wherein the elongated cross-section of the cylindrical segment is eight-shaped.

14. The apparatus of claim 12, wherein the drill guide includes an arm extending from the cylindrical segment, the arm forming an open channel supporting the tunnel-forming device.

15. The apparatus of claim 14, wherein the arm is a semi-cylindrical elongated member.

16. The apparatus of claim 14, further comprising a support member coupled to the arm and oriented at an angle relative to the arm.

* * * * *